(12) United States Patent
Chapoy et al.

(10) Patent No.: US 8,131,333 B2
(45) Date of Patent: Mar. 6, 2012

(54) OPHTHALMIC SENSOR

(75) Inventors: L. Lawrence Chapoy, Barrington Hills, IL (US); Angelika Maria Domschke, Duluth, GA (US); Dawn Smith, Duluth, GA (US)

(73) Assignee: EyeSense AG, Basel (CH)

( * ) Notice: Subject to any disclaimer, the term of this patent is extended or adjusted under 35 U.S.C. 154(b) by 1639 days.

(21) Appl. No.: 10/566,406

(22) PCT Filed: Aug. 6, 2004

(86) PCT No.: PCT/EP2004/008825
§ 371 (c)(1),
(2), (4) Date: Jul. 10, 2006

(87) PCT Pub. No.: WO2005/015237
PCT Pub. Date: Feb. 17, 2005

(65) Prior Publication Data
US 2007/0030443 A1 Feb. 8, 2007

Related U.S. Application Data

(60) Provisional application No. 60/493,241, filed on Aug. 7, 2003.

(51) Int. Cl.
*A61B 5/1455* (2006.01)
(52) U.S. Cl. .................. 600/319; 600/317; 600/321
(58) Field of Classification Search ............... 600/318, 600/319, 321
See application file for complete search history.

(56) References Cited

U.S. PATENT DOCUMENTS

| | | |
|---|---|---|
| 3,958,560 A | 5/1976 | March |
| 4,321,575 A | 3/1982 | Koszewa et al. |
| 4,632,844 A | 12/1986 | Yanagihara et al. |
| 5,527,925 A | 6/1996 | Chabrecek et al. |
| 5,535,743 A | 7/1996 | Backhaus et al. |
| 5,583,163 A | 12/1996 | Mueller |
| 5,665,840 A | 9/1997 | Poehlmann et al. |
| 5,712,356 A | 1/1998 | Bothe et al. |
| 5,849,841 A | 12/1998 | Muehlebach et al. |
| 6,165,408 A | 12/2000 | Steinmann |
| 6,221,303 B1 | 4/2001 | Steinmann |
| 6,303,687 B1 | 10/2001 | Mueller |
| 6,451,871 B1 | 9/2002 | Winterton et al. |
| 6,479,587 B1 | 11/2002 | Stockinger et al. |
| 2001/0026946 A1 | 10/2001 | Asher |
| 2001/0034500 A1* | 10/2001 | March .................. 600/319 |
| 2002/0049389 A1 | 4/2002 | Abreu |
| 2003/0045783 A1 | 3/2003 | March et al. |
| 2004/0087842 A1 | 5/2004 | Lakowicz et al. |

FOREIGN PATENT DOCUMENTS

| | | |
|---|---|---|
| EP | 0 632 329 B1 | 1/1995 |
| EP | 0 637 490 B1 | 2/1995 |
| EP | 0 655 470 B1 | 5/1995 |
| EP | 0 367 513 B1 | 7/1995 |
| EP | 0 712 867 B1 | 5/1996 |
| EP | 0 932 635 B1 | 8/1999 |
| EP | 0 958 315 B1 | 11/1999 |
| EP | 0 961 941 B1 | 12/1999 |
| WO | WO-87/04390 A1 | 7/1987 |
| WO | WO-00/78830 A1 | 12/2000 |
| WO | WO-01/13783 A1 | 3/2001 |
| WO | WO-02/087429 A1 | 11/2002 |
| WO | WO-03/031150 A1 | 4/2003 |

OTHER PUBLICATIONS

H. Shinmori et al., "Spectroscopic Sugar Sensing by a Stilbene Derivative with Push ($Me_2N$-)-Pull (($HO)_2B$)-Type Substituents," Tetrahedron, vol. 51, No. 7, (1995) pp. 1893-1902.

N. Dicesare et al., "Chalcone-analogue fluorescent probes for saccharides signaling using the boronic acid group," Tetrahedron Letters 43 (2002), pp. 2615-2618.

N. Dicesare et al., "Spectral Properties of Fluorophores Combining the Boronic Acid Group with Electron Donor or Withdrawing Groups, Implication in the Development of Fluorescence Probes for Saccharides," J. Phys. Chem. A, vol. 105, No. 28, 2001, pp. 6834-6840.

N. Dicesare et al., "Wavelength-ratiometric probes for saccharides based on donor-acceptor diphenylpolyenes," Journal of Photochemistry and Photobiology A: Chemistry, vol. 143, No. 1, 2001, pp. 39-47.

R. Badugu et al., "Noninvasive Continuous Monitoring of Physiological Glucose Using a Monosaccharide-Sensing Contact Lens," Analytical Chemistry, vol. 76, No. 3, Feb. 1, 2004, pp. 610-618.

N. Dicesare et al., "Charge transfer fluorescent probes using boronic acids for monosaccharide signaling," Journal of Biomedical Optics, vol. 7, No. 4, Oct. 2002, pp. 538-545.

V. V. Karnati et al., "A Glucose-Selective Fluorescence Sensor Based on Boronic Acid-Diol Recognition," Bioorganic & Medicinal Chemistry Letters 12, (2002), pp. 3373-3377.

* cited by examiner

*Primary Examiner* — Eric Winakur
(74) *Attorney, Agent, or Firm* — Fanelli Haag PLLC

(57) ABSTRACT

This invention is generally related to a biocompatible sensor for detecting/measuring sugar, especially glucose, in an ocular fluid in a non-invasive or minimally invasive manner and a method for using the biocompatible sensor. A biocompatible sensor of the invention comprises, consists essentially, or consists of an ophthalmic device comprising a molecular sensing moiety which interacts or, reacts with sugar to provide an optical signal which is indicative of sugar level in an ocular fluid.

11 Claims, No Drawings

OPHTHALMIC SENSOR

This application is a national stage filing under 35 U.S.C. 371 of International Application No. PCT/EP2004/008825 filed Aug. 6, 2004, which claims benefits under 35 U.S.C. 119(e) of U.S. Provisional Patent Application No. 60/493,241 filed Aug. 7, 2003.

The invention is related to an ophthalmic sensor which comprises an ophthalmic device having a polymer matrix and a molecular sensing moiety which interacts with sugar to provide an optical signal being indicative of sugar level in an ocular fluid. An ophthalmic sensor of the present invention is suitable for continuously monitoring of glucose concentration in a body fluid in a non-invasive or minimally invasive manner.

BACKGROUND OF THE INVENTION

Diabetes is a serious, lifelong disease which can cause long-term complications that affect almost every part of the body. This disease often leads to blindness, heart and blood vessel disease, strokes, kidney failure, amputations, and nerve damage. Uncontrolled diabetes can complicate pregnancy, and birth defects are more common in babies born to women with diabetes. Diabetes is widely recognized as one of the leading causes of death and disability in the United States.

One important aspect in the treatment of diabetes is the tight control of blood glucose levels, which requires frequent monitoring of blood glucose levels of patients so as to manage food intake and the dosage and timing of insulin injection. Tests for determining serum glucose concentration typically require blood collection. Blood collection is an invasive technique requiring arterial or venous puncture. A patient has to endure discomfort associated with needles or other devices to obtain blood samples for testing. Currently, millions of diabetics are forced to draw blood daily to determine their blood sugar levels. In addition, blood collection sometimes can be associated with problems in various ethnic settings. To alleviate the constant discomfort and inconvenience for these individuals, substantial effort has been expanded in the search for a non-invasive or minimally invasive technology to accurately determine blood glucose levels, in particular for a non-invasive or minimally invasive to continuously or at least frequently monitor blood glucose levels.

In recent years, various non-invasive and minimally-invasive technologies have been proposed in the academic and patent literature to monitor blood glucose levels by determining glucose concentrations in an ocular fluid, such as tears, aqueous humor, or interstitial fluid. For example, PCT International Publication WO 01/13783, discloses that an ophthalmic lens comprising a chemical sensor can be used to determine the amount of an analyte (e.g., glucose) in an ocular fluid, which is accessible to light. Such chemical sensors comprise a receptor specific for an analyte of interest and a detectable label (e.g., a fluorescent label) which in combination with the receptor to provide a detectable optical signal (e.g., fluorescent signal). Nevertheless, although these ophthalmic lenses of WO 01/13783 can be used in non-invasive or minimally-invasive monitoring of glucose level in a body fluid, a need for further improvement still remains, in particular need for incorporating highly sensitive chemical sensor systems into an ophthalmic device.

The primary object of the invention is to provide an ophthalmic sensor device containing a molecular sensing moiety which interacts with sugar to provide an optical signal being indicative of sugar level in an ocular fluid. Such molecular sensing moiety has a relatively high sensitivity for glucose sensing, a relatively high binding reversibility with glucose and relatively long shelf-life.

SUMMARY OF THE INVENTION

The invention provides an ophthalmic sensor, comprising, consisting essentially, or consisting of: an ophthalmic device having a polymer matrix and a molecular sensing moiety in and/or on said ophthalmic device, a molecular sensing moiety which interacts or reacts with sugar to provide an optical signal which is indicative of sugar level in an ocular fluid.

This and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF PREFERRED EMBODIMENTS

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

"Biocompatible", as used herein, refers to a material or a surface of a material or an article which does not deteriorate appreciably and does not induce a significant immune response or deleterious tissue reaction, e.g., toxic reaction or significant irritation, over time when implanted into or placed adjacent to the biological tissue of a subject. Preferably, a biocompatible material does not deteriorate and does not cause immune response or deleterious tissue reaction over at least 6 months, more preferably at least 1 year, most preferably at least 10 years. Exemplary biocompatible materials that are particularly suitable for producing a biocompatible sensor of the present invention are discussed below.

An "ophthalmic device", as used herein, refers to a contact lens (hard or soft), a corneal onlay, implantable ophthalmic devices used in, on or about the eye or ocular vicinity.

An "implantable ophthalmic device", as used herein, refers to an ophthalmic device which is used in, on or about the eye or ocular vicinity. Exemplary implantable ophthalmic devices include, without limitation, an intraocular lens, a subconjunctival lens, an intracorneal lens, and a shunt or implant (e.g., a stent, or a glaucoma shunt or the like) that can rest in the cul de sac of an eye.

The term "contact lens" employed herein in a broad sense and is intended to encompass any hard or soft lens used on the eye or ocular vicinity for vision correction, diagnosis, sample collection, drug delivery, wound healing, cosmetic appearance (e.g., eye color modification), or other ophthalmic applications.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) and/or conjunctiva which may come into intimate contact with a contact lens.

A "hydrogel material" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, silicone-containing hydrogels, polyurethane, polyurea, and the like. A hydrogel can be prepared according to any methods known to a person skilled in the art.

A "lens-forming material" refers to a material which can be polymerized and/or crosslinked by actinic radiation to form a contact lens. A lens-forming material can be any materials known to a skilled artisan. For example, a lens-forming material can be a prepolymer, a mixture of prepolymers, a mixture of monomers, or a mixture of one or more prepolymers and one or more monomers and/or macromers. A lens-forming material can further include other components, such as a photoinitiator, a visibility tinting agent, UV-blocking agent, photosensitizers, and the like.

Actinic radiation refers to radiation of a suitable form of energy. Examples of actinic radiation includes without limitation light radiation (e.g., UV radiation), gamma radiation, electron radiation, X-ray irradiation, microwave irradiation, thermal radiation and the like.

A "monomer" means a low molecular weight compound that can be polymerized. Low molecular weight typically means average molecular weights less than 700 Daltons.

A "hydrophilic vinylic monomer" refers to a monomer which as a homopolymer typically yields a polymer that is water-soluble or can absorb at least 10 percent by weight water.

A "macromer" refers to medium and high molecular weight compounds or polymers that contain functional groups capable of further polymerization. Medium and high molecular weight typically means average molecular weights greater than 700 Daltons.

"Molecular weight" of a polymeric material (including monomeric or macromeric materials), as used herein, refers to the number-average molecular weight unless otherwise specifically noted or unless testing conditions indicate otherwise.

A "polymer" means a material formed by polymerizing one or more monomers.

A "prepolymer" refers to a starting polymer which can be polymerized and/or crosslinked upon actinic radiation to obtain a crosslinked polymer having a molecular weight much higher than the starting polymer.

A "photoinitiator" refers to a substance that can initiate free radical polymerization and/or crosslinking by the use of light. Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®. Examples of benzoylphosphine initiators include 2,4,6-trimethylbenzoyidiphenylo-phosphine oxide; bis-(2,6-dichlorobenzoyl)-4-N-propylphenylphosphine oxide; and bis-(2,6-dichlorobenzoyl)$_4$-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

A "visibility tinting agent" refers to a substance that dyes (or colors) a contact lens to enable a user to easily locate a contact lens in a clear solution within a lens storage, disinfecting or cleaning container. It is well known in the art that a dye and/or a pigment can be used as a visibility tinting agent.

A "dye" means a substance that is soluble in a solvent and that is used to impart color. Dyes are typically translucent and absorb but do not scatter light. Any suitable biocompatible dye can be used in the present invention.

A "Pigment" means a powdered substance that is suspended in a liquid in which it is insoluble. A pigment can be a fluorescent pigment, phosphorescent pigment, pearlescent pigment, or conventional pigment. While any suitable pigment may be employed, it is presently preferred that the pigment be heat resistant, non-toxic and insoluble in aqueous solutions. Examples of preferred pigments include (C.I. is the color index no.), without limitation, for a blue color, phthalocyanine blue (pigment blue 15:3, C.I. 74160), cobalt blue (pigment blue 36, C.I. 77343), Toner cyan BG (Clariant), Permajet blue B2G (Clariant); for a green color, phthalocyanine green (Pigment green 7, C.I. 74260) and chromium sesquioxide; for yellow, red, brown and black colors, various iron oxides; PR122, PY154, for violet, carbazole violet; for black, Monolith black C-K (CIBA Specialty Chemicals).

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating that is not covalently attached to a medical device and is obtained through a layer-by-layer ("LbL") deposition of polyionic materials on an article. Any suitable LbL polyelectrolyte deposition techniques can be used in the LbL coating. For example, U.S. Pat. No. 6,451,871, issued to Winterton et al, discloses an LbL polyelectrolyte deposition technique that involves consecutively dipping a substrate into oppositely charged polyionic materials until a coating of a desired thickness is formed.

The term "bilayer" is employed herein in a broad sense and is intended to encompass, a coating structure formed by applying one layer of a first polyionic material and subsequently one layer of a second polyionic material having charges opposite of the charges of the first polyionic material. It should be understood that the layers of the first and second polyionic materials may be intertwined with each other in the bilayer.

A "charged polymeric material" or a "polyionic material" refers to a charged polymer that has a plurality of charged groups in a solution, or a mixture of charged polymers each of which has a plurality of charged groups in a solution. Exemplary charged polymers includes polyelectrolytes, p- and n-type doped conducting polymers. Charged polymeric materials include both polycationic (having positive charges) and polyanionic (having negative charges) polymeric materials.

The term "molecular sensing moiety" employed herein in a broad sense and is intended to encompass, for example, a chemical or biochemical molecule or fragments thereof that is capable of interacting or reacting specifically with an analyte of interest in a sample to provide one or more optical signal. Exemplary molecular sensing moieties includes without limitation derivatives of phenyl boronic acid (for interacting with glucose), a receptor for specifically binding an analyte of interest, and an enzyme which reacts specifically with an analyte of interest.

Naturally, boronic acid compounds have been used for the synthesis of glucose sensors. Boronic acids are weak Lewis Acids composed of an electron deficient boron atom and two hydroxyl groups, which can interact with strong bases like OH— to from the anionic borate form, showing typically high pKa around 9 (Karnati, et al., A glucose-selective fluorescence sensor based on boronic acid-diol recognition, Bioorganic and Medicinal Chemistry Letters, 12, (2002), 3373-3377; Dicesare and Lakowicz, Charge transfer fluorescent probes using boronic acids for monosaccharide signaling, J. Biomedical Optics, 7(4), (2002), 538-545, incorporated herein by reference in their entirety). Boronic acids couple with diols to form a boronic acid diester group. The diol is linked covalently, and the reaction is fast and completely reversible. In comparison to the boronic acid group, the boronic acid ester group shows higher acidity (pKa ~6) due to a higher electrophilic boron atom. The phenylboronic acid group shows higher affinity for D-fructose with a smaller affinity for D-glucose, with binding constants of ~0.5 and 10 mM respectively (Dicesare and Lakowicz, Charge transfer fluorescent probes using boronic acids for monosaccharide signaling, J. Biomedical Optics, 7(4), (2002), 538-545, incorporated herein by reference in its entirety). The use of the boronic acid groups for sensing sugars is strongly dependent on the molecular geometry and the aromatic species where the boronic acid group is present, hence glucose sensitive probes can be made with a variety of affinities, in the mM range for blood glucose, and in the µM range for tear glucose.

Examples of optical signals include changes in the optical properties, including, but not limited to, a change in color, changes in intensity (absorbance or fluorescence) at different wavelengths, a spectral (absorption or emission) shift, changes in lifetime of luminescence (fluorescence, phosphorescence, and the like), and the like. A change in color can be observed by naked eyes and can be used in qualitative or semi-quantitative assays.

The term "receptor" employed herein in a broad sense and is intended to encompass, for example, a protein or fragment thereof or a biochemical compound that is capable of binding an analyte of interest in a sample. Exemplary receptors include, without limitation, antibodies or fragments thereof, lectins or fragments thereof, hormone receptors or fragments thereof, drug receptors or fragment thereof, enzymes or fragment thereof, aptamers, nucleic acids, nucleic acid analogs, and the like.

This invention is generally related to a biocompatible sensor for detecting/measuring sugar, in particular glucose, in a body fluid and a method for using the biocompatible sensor. A biocompatible sensor of the invention comprises, consists essentially, or consists of an ophthalmic device including a polymer matrix and a molecular sensing moiety in and/or on the ophthalmic device. The molecular sensing moiety is a phenyl boronic acid containing a fluorophore moiety and can interact or react specifically with sugar to provide an optical signal which is indicative of the sugar level in a body fluid. The polymer matrix is formed by polymerizing/crosslinking a lens forming material according to a method known to a person skilled in the art.

In accordance with the present invention, an ophthalmic device is a contact lens (hard or soft), a corneal onlay, implantable ophthalmic devices used in, on or about the eye or ocular vicinity.

A contact lens can be a hard or soft contact lens. It can be a daily-disposable contact lens, a daily-wear contact lens or an extended-wear contact lens. A contact lens as an ophthalmic sensor device of the invention can be made from any known suitable lens-forming materials. For example, a lens-forming material can be a prepolymer, a mixture of prepolymers, a mixture of monomers, or a mixture of one or more prepolymers and one or more monomers and/or macromers. A lens-forming material can further include other components, such as a photoinitiator, a visibility tinting agent, UV-blocking agent, photosensitizers, and the like. It should be understood that any silicone-containing prepolymers or any silicone-free prepolymers can be used in the present invention.

A preferred group of lens-forming materials are prepolymers which are water-soluble and/or meltable. It would be advantageous that a lens-forming material comprises primarily one or more prepolymers which are preferably in a substantially pure form (e.g., purified by ultrafiltration). Therefore, after crosslinking/polymerizing by actinic radiation, a contact lens may require practically no more subsequent purification, such as in particular complicated extraction of unpolymerized constituents. Furthermore, crosslinking/polymerizing may take place solvent-free or in aqueous solution, so that a subsequent solvent exchange or the hydration step is not necessary.

Examples of preferred prepolymers include, but are not limited to, a water-soluble crosslinkable poly(vinyl alcohol) prepolymer described in U.S. Pat. Nos. 5,583,163 and 6,303,687 (incorporated by reference in their entireties); a water-soluble vinyl group-terminated polyurethane which is obtained by reacting an isocyanate-capped polyurethane with an ethylenically unsaturated amine (primary or secondary amine) or an ethylenically unsaturated monohydroxy compound, wherein the isocyanate-capped polyurethane can be a copolymerization product of at least one polyalkylene glycol, a compound containing at least 2 hydroxyl groups, and at least one compound with two or more isocyanate groups; derivatives of a polyvinyl alcohol, polyethyleneimine or polyvinylamine, which are disclosed in U.S. Pat. No. 5,849,841 (incorporated by reference in its entirety); a water-soluble crosslinkable polyurea prepolymer described in U.S. Pat. No. 6,479,587 (herein incorporated by reference in its entirety); crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635; branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in PCT patent application WO 2000/31150.

An ophthalmic lens of the invention may be produced by any convenient manufacturing means, including, for example, a computer-controllable manufacturing device, molding or the like. A "computer controllable manufacturing device" refers to a device that can be controlled by a computer system and that is capable of producing directly an ophthalmic lens or optical tools for producing an ophthalmic lens. Any known, suitable computer controllable manufacturing device can be used in the invention. Exemplary computer controllable manufacturing devices includes, but are not limited to, lathes, grinding and milling machines, molding equipment, and lasers.

Preferably, contact lenses can be manufactured economically in large numbers by a conventional full-mold process involving disposable molds, the examples of which are disclosed in, for example, PCT patent application no. WO/87/04390 or in EP-A 0 367 513 (herein incorporated by reference in their entireties). More preferably, contact lenses can be manufactured economically in large numbers by a process described in European Patent EP 0 637 490 B1 (herein incorporated by reference in its entirety). In the process of EP 0 637 490 B1, a lens-forming material (e.g., a prepolymer solution) is introduced into a mold consisting of two mold halves, the two mold halves not touching each other but having a thin gap of annular design arranged between them. The gap is connected to the mold cavity, so that excess lens forming material can flow away into the gap. The crosslinking of the lens-forming material is carried out by means of actinic irradiation, especially with UV light, the irradiation of the mold cavity being spatially limited by means of a chromium mask. Thus, only the lens-forming material which is in the unmasked area in the mold cavity is crosslinked, whereas the lens-forming material located in the masked area (behind the mask, such as in the gap, so that high reproducibility of the rim shaping of the lens can be achieved without a positive connection between the two mold halves made of polypropylene or polystyrene. The uncrosslinked, shadowed prepolymer solution can easily be washed away from the dimensionally stable, crosslinked lens by using water. Instead of polypropylene or polystyrene molds that can be used only once, it is possible for reusable quartz/glass molds or reusable plastic molds to be used, since, following the production of a lens, these molds can be cleaned rapidly and effectively off the uncrosslinked prepolymer and other residues, using water, on account of the water-soluble basic chemistry, and can be dried with air. By this means, molding of contact lenses with high precision and reproducibility can in particular be achieved.

A contact lens of the invention can be used in non-invasively monitoring of glucose levels in tears. Glucose levels in tears then can be converted into blood glucose levels based on correlations between tear glucose levels and blood glucose levels.

An ophthalmic sensor device can be an implantable ophthalmic device. Glucose levels in tears may be much lower than blood glucose levels. With an implantable ophthalmic sensor device of the invention, one can monitor periodically or on demand glucose levels in aqueous humor or interstitial fluid where glucose levels can be much higher than glucose levels in tears. Preferably, an implantable ophthalmic sensor device of the invention is a subconjunctival implant, an intracoenal lens, a stent, or a glaucoma shunt. An implantable ophthalmic device can be produced according to any known suitable methods.

A molecular sensing moiety can be physically bond or covalently linked to a polymer matrix prepared from a crosslinkable and/or polymerizable fluid material, according to any known, suitable methods. For example, a prepolymer and a molecular sensing compound, which comprises or be modified to comprise matching functional groups, can be covalently linked with each other, thereby incorporating molecular sensing moiety into the modified prepolymer.

A molecular sensing moiety can also be covalently attached to the ophthalmic device to form an ophthalmic sensor of the invention. Such ophthalmic sensor can be prepared by first functionalizing the surface of a preformed ophthalmic device to obtain-function groups and then covalently attaching a layer of a molecular sensing moiety. Surface modification (or functionalization) of an ophthalmic device is well known to a person skilled in the art. Any known suitable method can be used.

For example, the surface modification of a contact lens includes, without limitation, the grafting of monomers or macromers onto polymers to make the lens biocompatible, wherein monomers or macromers contain functional groups, for example, such as hydroxyl group, amine group, amide group, sulfhydryl group, —COOR (R and R' are hydrogen or $C_1$ to $C_8$ alkyl groups), halide (chloride, bromide, iodide), acyl chloride, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, hydroxysuccinimide ester, hydroxysulfosuccinimide ester, imido ester, hydrazine, axidonitrophenyl group, azide, 3-(2-pyridyl dithio)proprionamide, glyoxal, aldehyde, epoxy. The above mentioned functional groups can alternatively be introduced onto the surface of a contact lens by using other surface modification techniques, such as, for example, a surface treatment by energy (e.g., a plasma, a static electrical charge, irradiation, or other energy source), chemical treatments, or layer-by-layer deposition of polyelectrolytes (LbL coating).

It is well known in the art that a pair of matching functional groups can form a covalent bond or linkage under known reaction conditions, such as, oxidation-reduction conditions, dehydration condensation conditions, addition conditions, substitution (or displacement) conditions, 2+2 cyclo-addition conditions, Diels-Alder reaction conditions, ROMP (Ring Opening Metathesis Polymerization) conditions, vulcanization conditions, cationic crosslinking conditions, and epoxy hardening conditions. For example, an amino group is covalently bondable with aldehyde (Schiff base which is formed from aldehyde group and amino group may further be reduced); an hydroxyl group and an amino group are covalently bondable with carboxyl group; carboxyl group and a sulfo group are covalently bondable with hydroxyl group; or a mercapto group is covalently bondable with amino group.

Exemplary covalent bonds or linkage, which are formed between pairs of crosslinkable groups, include without limitation, ester, ether, acetal, ketal, vinyl ether, carbamate, urea, amine, amide, enamine, imine, oxime, amidine, iminoester, carbonate, orthoester, phosphonate, phosphinate, sulfonate, sulfinate, sulfide, sulfate, disulfide, sulfinamide, sulfonamide, thioester, aryl, silane, siloxane, heterocycles, thiocarbonate, thiocarbamate, and phosphonamide.

Exemplary functional groups include hydroxyl group, amine group, amide group, sulfhydryl group, —COOR (R and R' are hydrogen or $C_1$ to $C_8$ alkyl groups), halide (chloride, bromide, iodide), acyl chloride, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, hydroxysuccinimide ester, hydroxysulfosuccinimide ester, imido ester, hydrazine, axidonitrophenyl group, azide, 3-(2-pyridyl dithio)proprionamide, glyoxal, aldehyde, epoxy.

It is understood that coupling agents may be used. Coupling agents useful for coupling antimicrobial peptide to the LbL coating of a medical device include, without limitation, N. N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl) carbodiimide, diisopropyl carbodiimide, or mixtures thereof. The carbodiimides also may be used with N-hydroxysuccinimide or N-hydroxysulfosuccinimide to form esters that can react with amines to form amides.

Alternatively, a molecular sensing moiety can be incorporated in a vinylic monomer which is one of the components of a crosslinkable and/or polymerizable fluid material.

Examples of preferred derivatives of phenyl boronic acid include, without limitation, those having the following structural formula (1) or (2):

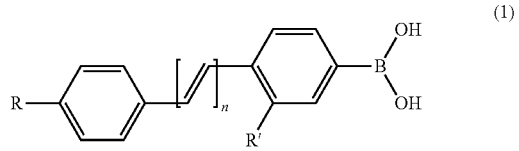

(1)

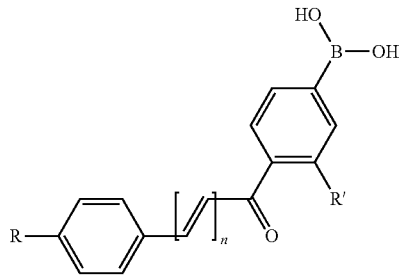

(2)

wherein
R' is H or an olefinically unsaturated, crosslinkable radicals, preferably having up to 25 carbon atoms;
R is H, $NR_1R_2$, CN, $OCH_3$, or a radical constituent capable of donating an electron to or accepting an electron from adjacent aromatic system, wherein $R_1$ is H or $C_1$-$C_6$ alkyl, and $R_2$ is a $C_3$-$C_{25}$ radical terminated with

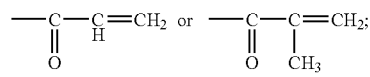

and
n is an integer from 1 to 5.

It is understood that the phenyl ring of a derivative of phenyl boronic acid can be substituted with electron withdrawing groups such as fluorine or nitrate and that the position of the boronic acid may vary.

One preferred example of R' in formula (1) or (2) is

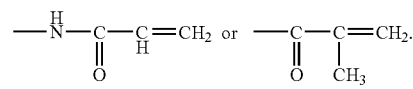

A derivative of phenyl boronic acid of formula (1) or (2) having an olefinically unsaturated, crosslinkable radical can be incorporated in a lens-forming material for making an ophthalmic sensor device of the invention. In this case, a molecular sensing moiety can be copolymerized with other polymerizable components in the lens-forming material and thereby become parts of or be anchored onto the polymer matrix of the ophthalmic device.

Where a derivative of phenyl boronic acid of formula (1) or (2) without any olefinically unsaturated, crosslinkable radical, it can be entrapped in the polymer matrix by incorporating it in a lens-forming material before curing.

A derivative of phenyl boronic acid of formula (1) or (2) can interact or react with a sugar, preferably glucose, to cause changes in fluorescence lifetime, changes in fluorescence intensity, and/or spectral shifts. Any known suitable methods for measuring fluorescence intensity, and spectral shifts can be used in the invention to determine glucose concentration in an ocular fluid.

The previous disclosure will enable one having ordinary skill in the art to practice the invention. In order to better enable the reader to understand specific embodiments and the advantages thereof, reference to the following examples is suggested.

Example 1

This example illustrates boronic acid containing fluorophores (BAFs) which employ different mechanisms to induce spectral changes in the presence of sugar, in particular excited-state charge transfer (CT). CT is a versatile mechanism that can be applied to a large number of fluorophores, where the boronic acid group and an electron donor group are present on the same fluorophore. Here, the BA group [—B(OH)2] acts as an electron withdrawing group. However, in the presence of sugar and at an appropriate pH, the boronic acid group is present in its anionic form, namely [—B(OH)(Sugar)]- and is no longer an electron withdrawing group. Hence spectral changes can be observed due to the perturbation of the charge transfer nature of the excited state. Here we employ this mechanism with a range of probes of formula (1) and (2), in which R' is H, R is $N(CH_3)_2$, or CN and n is 1 or 2, for glucose sensing within a contact lens. These probes show both wavelength shifts and intensity changes towards glucose within the contact lens, demonstrating a strong future potential for the non-invasive monitoring of tear glucose and therefore blood glucose. In addition, spectral data obtained from the contact lens with bulk solution based measurements are compared, in an attempt to optimize sensor response with regard to leaching, pKa and the dynamic range for sensing.

All chemicals are purchased from Sigma. The preparation of the BAFs is in accordance with those described in articles, Tetrahedron Letters, 43, (2002), 2615-2618 and J. Biomedical Optics, 7(4), (2002), 538-545 (Incorporated by reference in their entireties).

The contact lenses are Focus Dailies® lenses (Nelfilcon A, CIBA Vision, Atlanta, USA), and are stirred in 500 ml water, 20° C. for 24 hrs before post-doping. The contact lens is a polyvinyl alcohol based polymer which swells slightly in water. Its hydrophilic character readily allows for the diffusion of the aqueous analytes in tears.

Doping is undertaken by incubating the lenses in a high concentration of the respective BAFs solution for 24 hrs before being rinsed in Millipore water. Lenses are used directly after been prepared.

All solution fluorescence measurements are undertaken in 4×1×1 cm fluorometric plastic cuvettes, using a Varian fluorometer.

Doped contact lenses are mounted in a custom made (CIBA Vision) lens holder, which is itself inserted into a quartz holder for fluorescence sensing measurements. Excitation and emission is performed using a Varian Fluorometer; a geometry, wherein the concave edge of the lens faces towards the excitation source, is employed to reduce any scattering of the excitation light. We additionally tested the lens excited from the convex edge, just as would be used in the eye, and found identical results.

The quartz lens holder has dimensions of 4*2.5*0.8 cm, all 4 sides being of optical quality. The contact lens is mounted onto a stainless steel mount of dimensions 4*2*0.4 cm which fits tightly within the quartz outer holder. A circular hole in the center of the mount with a 2.5 cm ID, has a raised quartz lip, which enables the lens to be mounted. The mount and holder readily allow for ~1.5 $cm^3$ of solution to be in contact with the front and back sides of the lens for the sugar sensing experiments.

Leaching of the probes from the contact lens polymer is observed using the sample holder, which contained ~1.5 $cm^3$ buffer, at 20° C. A Varian fluorometer measured the intensity change as a function of time to determine the percentage signal change, corresponding to dye leaching. It should be noted that with no sample present, no intensity fluctuations or drifts are observed, indicating stability of the fluorometer Xenon-arc source.

To determine the usefulness of BAFs with regard to tear glucose sensing in a contact lens, it is necessary to compare both solution and lens based measurements.

In Solution

Stilbene Derivatives. Two stilbene derivatives, 4'-Dimethylaminostilbene-4-boronic acid (DSTBA) and 4'-Cyanostilbene-4-boronic acid (CSTBA) are used. The dimethylamino group is an electron-donating group. Cyano group is an electron withdrawing group. These two probes demonstrating both reduced and increased CT respectively in the presence of sugar.

In the case of DSTBA in solution, it is found that the emission spectrum shows a hypsochromic shift of about 30 nm and an increase in fluorescence intensity as the concentration of fructose increases. These dramatic and useful changes can simply be explained by the loss of the electron withdrawing property of the boronic acid group following the formation of the anionic form.

In the case of CSTBA stilbene derivative having two electron withdrawing groups, in the presence of sugar a bathochromic shift, some 25 or so nm, and a decrease in the intensity at pH 8, is observed. These results are opposite to that observed for DSTBA. This change has been attributed to an excited CT state present for the anionic form of CSTBA, where no CT states are observed for the neutral form of the boronic acid group, suggesting that the anionic form of the boronic acid group can act as an electron donor group.

It is observed that for both stilbene probes they have higher affinities for D-Fructose and that the affinity decreases for D-Galactose and D-Glucose.

Polyene Derivative. In order to test the suitability of longer wavelength probes in the contact lens, a polyene derivative, DDPBBA, 1-(p-Boronophenyl)-4-(p-dimethylaminophenyl) buta-1,2-deine, which combined a dimethylamino group and a boronic acid group in the para positions of each of the phenyl groups. As observed for DSTBA, there are a blue shift in the emission and an increase in the emission intensity with increasing sugar concentrations.

Chalcone Derivatives. Chalcone derivatives, unlike the stilbenes and polyenes, have the advantage of much longer wavelength emission. This is particularly attractive as longer wavelength emission reduces the detection of any lens or eye autofluorescence as well as scatter ($\lambda^{-4}$ dependence), and also allows the use of cheaper and longer wavelength laser or light emitting diode excitation sources, reducing the need for UV excitation in the eye. Two Chalcone derivatives, Chalc 1 (R=$N(CH_3)_2$, n=1 in formula (2)) and Chalc 2 (R=$N(CH_3)_2$, n=2 in formula (2)), are prepared according to the procedures described in Tetrahedron Letters, 43, (2002), 2615-2618 and J. Biomedical Optics, 7(4), (2002), 538-545 (Incorporated by reference in their entireties). For these probes, the boronic acid group does not produce resonance forms with the electron donating amino group. The CT occurs between the dimethylamino group (electron donating group) and the carbonyl group (electron withdrawing group). Upon sugar binding to the boronic acid group, then a change in the electronic properties of the boron group, both when free and when complexed with sugar, leads to a change in the electronic density of the benzophenone moiety and subsequently the CT properties of the excited state of the fluorophore, noting that boronic acid. group is in resonance with the carbonyl group. Both Chalcone derivatives show a similar response to sugar and pH.

In Contact Lens

Doped contact lenses, which are previously washed and allowed to leach excess dye for 1 hr, are inserted in the contact lens holder. Buffered solutions of sugars are then added to the lens, which are also similarly buffered in the 1.5 cm³ cell volume. Fluorescence spectra are typically taken 15 mins after each sugar addition to allow the lens to reach equilibrium.

Stilbene Derivatives. Results show response of a DSTBA doped contact lens towards both glucose and fructose. The magnitude of the response towards fructose is greater, reflecting the higher affinity of mono boronic acids for fructose. Comparing the response of DSTBA in both solution and lens, it is noticed that an opposite response is observed in the lens, where the emission spectra similarly shows a blue shift, accompanied by a decrease in intensity as the fructose concentration is increased. In addition the sugar affinity is decreased slightly in the lens.

Results also show the response of CSTBA in the lens for both glucose and fructose. While a similar reduction in intensity is observed as compared to solution, no red shift in the emission is observed, indicative of a reduction in the electron donating capability of the anionic sugar bound form.

The lack of suitable spectral shifts in the presence of sugar eliminates, at this stage, the possibility of wavelength ratiometric sensing.

Comparing the responses of the stilbene probes based on a simple intensity ratio measurement, it is interesting to see the much greater response for fructose for CSTBA in the lens as compared DSTBA, where notable changes in intensity occur at <20 mM [fructose]. However the glucose response of DSTBA in the contact lens appears more promising for [glucose]<10 mM, where a 10% fluorescence intensity change is observed for ~10 mM glucose at pH 8.0.

Polyene Derivative. The spectral response of DDPBBA in the contact lens is also different to that observed in solution. A decrease in intensity is typically observed for increasing sugar concentration, and a slight blue shift is evident for fructose binding. This is in contrast to solution-based responses which show both a blue shifted and increased emission. While the general spectral changes observed for both DSTBA and DDPBBA, are similar, a greater dynamic response to sugar is observed for DSTBA as compared to DDPBBA. In addition, the response of DDPBBA towards both glucose and fructose are similar over the sugar concentration range studied, as compared to the significantly different responses observed for both sugars for DSTBA and CSTBA.

Chalcone Derivatives. The response of Chalc 1 and Chalc 2 doped contact lenses display similar responses to sugar, only their respective emission wavelengths differ. Chalc 1 shows an emission centered around 560 nm in the lens as compared to 580 nm in solution, while Chalc 2 shows an emission centered at ~630 nm as compared to 665 nm in solution. In contrast to the responses observed in solution, a reduction in fluorescence intensity is observed for both Chalc 1 and 2 doped contact lenses. Interestingly, the solution response for Chalc 2 towards 100 mM fructose at pH 8.0 produces an ~3 fold increase in fluorescence emission, as compared to the ~2.6 fold reduction for the same fructose concentration in the contact lens.

Probe Leaching from the Contact Lens

To ascertain the practical use of a glucose sensing contact lens, leaching studies of the probes from within the lens are undertaken. Due to the very low concentration of probes within the lens, absorbance measurements could not be used to track the amount of unleached dye. Subsequently, we tracked the % loss of fluorescence emission from the lens as a function of time. While it could be argued that this method is problematic, for example, dye could have a different quantum yield inside and outside the lens, this method is used to simply give an indication of how long we needed to pre-leach the lenses before use, as well as to provide general, information on the dye-lens compatibility.

Leaching experiments are also performed in the presence of sugar. Similar leaching rates are observed for the BAFs-sugar complexes.

Comparison Between in Solutions and in Contact Lenses

It is found that the response of the BAFs is notably different in the lens as compared to solution, although given their spectral differences alone, then this doesn't preclude their use in a glucose sensing contact lens.

For most of the BAFs studied, the response to sugars in the lens is opposite to that observed in solution. To understand these changes and therefore characterize the contact lens environment for further sensor development, the response of the BAFs in solution in both different pH and polarity media are assessed. Interestingly, we are able to observe a similar spectral response to glucose in pH 6.0 media as compared to the contact lens, although the wavelength emission maxima are somewhat different, suggesting more than just a pH effect. At this pH it is thought that the sugar bound form would be dominant, pKa ~6. Indeed, in a study of all the probes in both solution and in the contact lens, the observed lens responses are not identical to those observed in any pH solution, again suggesting an addition effect is also playing a role on the BAFs spectral response to sugar in the contact lens. To investigate lens pH further we doped a contact lens with the well-known pH sensitive probe, fluorescein, and measured the fluorescein lifetimes in the lens, determined using the time-correlated single photon counting technique and the experimental geometry mentioned before. A comparison with the lifetimes obtained for fluorescein in different pH buffers led us to conclude a lens pH in the range 5.5-6.5. Surprisingly, externally buffering the lens had little effect on the fluorescein lifetime and therefore lens pH. While it could be argued that fluorescein could sample a different micro region of the lens, not accessible too external buffer, our fluorescein pH lens results are also consistent with the BAFs lens results, which all have different molecular structures and are also likely to probe different lens micro domains. Indeed, the leaching results have shown different BAFs diffusion rates, suggesting diffusion from different micro domains, given that the molecular structures and therefore solution diffusion rates are likely to be similar. Hence there is strong evidence for a contact lens pH in the range 5.5-6.5.

To assess the polarity within the contact lens also, we measured the intensity ratio of the 0,0 (or 11) and 0,2 (or 13) bands of a pyrene doped lens, where the intensity ratio of pyrene fluorescence bands is widely used to estimate the polarity of media, such as in micelles. The lens is post-doped with pyrene by immersing the lens in a pyrene buffer methanol solution (pH 8.0, 2:1 v/v) for 1 hr. then rinsed extensively with Millipore water. The estimated value of $11-\frac{1}{3}$ is ~1.28, indicating the polarity within the lens is not indifferent than that of methanol (111 13 for MeOH=1.33). In retrospect, this is not surprising given that the contact lens is PVA based.

By determining both the pH and polarity within the contact lens it is possible to rationale the different spectral responses observed as compared to solution. As the solution pH increases the emission spectrum of DDPBBA displays a large blue shift. These spectral changes induced by the pH are due to the formation of the anionic form of the boronic acid group. As the anionic boronate species is formed, the boron group is no longer an electron-withdrawing group, resulting in the removal and/or perturbation of the charge transfer nature of the excited state. An important feature here is the change in acidity (electrophilicity) of the boron group between the uncomplexed and complexed forms. Indeed this acidity change is the driving force enabling the use of the boronic acid moiety for sugar sensing. At a lower pH (such as in the contact lens), the simple complexation of the boronic acid with sugar does not fully result in a perturbation of the fluorophore, hence DDPBBA is not suitable as a wavelength ratiometric probe in the contact lens. The same however would be true at a much higher pH also. To induce a spectral change of the fluorophore, the complexation of the BAFs with sugar should result in a perturbation of the electronic properties of the fluorophore, i.e. from the neutral to the anionic form. It is believed that these BAFs typically display pKa around 9, with a pKa ~6 for the sugar complexed form. Hence these probes are ideal for solution sugar sensing in the pH range 6.5-8.5, which for blood glucose levels is ideal, where the maximum spectral change is usually observed in the pH range 7-7.5. However, the low pH nature of the contact lens limits the spectral changes and therefore the dynamic range for tear glucose sensing. In addition these probes are polarity sensitive. For DSTBA and DDPBBA, as the polarity of the solvent increases, a red-shifted emission band can be observed, which accounts for the emission maximum difference between DDPBBA in the contact lens and in pH 6 solution. Similar rationale can also be drawn for the other BAFs considered here.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. An ophthalmic sensor, comprising an ophthalmic device having a polymer matrix and a molecular sensing moiety in and/or on said ophthalmic device, wherein the molecular sensing moiety is capable of interacting or reacting with sugar to provide an optical signal which is indicative of sugar level in an ocular fluid, wherein the molecular sensing moiety is a compound having a structural formula (1):

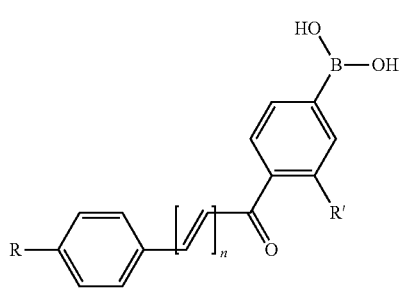

(1)

wherein R' is H or an olefinically unsaturated, crosslinkable radical having up to 25 carbon atoms; R is H, $NR_1R_2$, CN, $OCH_3$, or a radical constituent capable of donating an electron to or accepting an electron from an adjacent aromatic system, wherein $R_1$ is H or $C_1$-$C_6$ alkyl and $R_2$ is a $C_3$-$C_{25}$ radical terminated with:

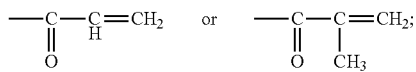

and n is an integer from 1 to 5.

2. The ophthalmic sensor of claim 1, wherein the ophthalmic device is a contact lens, a corneal onlay or an implantable ophthalmic device.

3. The ophthalmic sensor of claim 1, wherein the polymer matrix is obtained by polymerization of a material forming the ophthalmic device.

4. The ophthalmic sensor of claim 3, wherein the material forming the ophthalmic device comprises one or more prepolymers.

5. The ophthalmic sensor of claim 4, wherein the one or more prepolymers are silicone-containing prepolymers, silicone-free prepolymers, or a mixture thereof.

6. The ophthalmic sensor of claim 3, wherein the material forming the ophthalmic device comprises a mixture of monomers and optionally a macromer; or a mixture of one or more prepolymers with one or more monomers and/or macromers.

7. The ophthalmic sensor of claim 1, wherein R' is an olefinically unsaturated, crosslinkable radical having up to 25 carbon atoms.

8. The ophthalmic sensor of claim 7, wherein R is $NR_1R_2$, and wherein $R_1$ is H or $C_1$-$C_6$ alkyl and $R_2$ is a $C_3$-$C_{25}$ radical terminated with

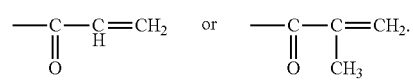

9. The ophthalmic sensor of claim 8, wherein the molecular sensing moiety is covalently attached to the surface of the ophthalmic device.

10. The ophthalmic sensor of claim 1, wherein R is $NR_1R_2$, and wherein $R_1$ is H or $C_1$-$C_6$ alkyl and $R_2$ is a $C_3$-$C_{25}$ radical terminated with

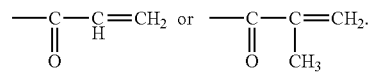

11. The ophthalmic sensor of claim 1, wherein the molecular sensing moiety is covalently attached to the surface of the ophthalmic device.

* * * * *